United States Patent
Su et al.

(10) Patent No.: US 11,340,203 B2
(45) Date of Patent: May 24, 2022

(54) TUNNEL TOXIC-AND-HARMFUL-GAS DEEP-HOLE DETECTION DEVICE AND METHOD

(71) Applicants: Chengdu Sudu Geological Engineering Consulting Co., Ltd., Chengdu (CN); Southwest Petroleum University, Chengdu (CN)

(72) Inventors: Peidong Su, Sichuan (CN); Peng Qiu, Chengdu (CN)

(73) Assignees: CHENGDU SUDU GEOLOGICAL ENGINEERING CONSULTING CO., LTD., Chengdu (CN); SOUTHWEST PETROLEUM UNIVERSITY, Chengdu (CN)

( * ) Notice: Subject to any disclaimer, the term of this patent is extended or adjusted under 35 U.S.C. 154(b) by 57 days.

(21) Appl. No.: 16/990,710

(22) Filed: Aug. 11, 2020

(65) Prior Publication Data

US 2021/0048419 A1   Feb. 18, 2021

(30) Foreign Application Priority Data

Aug. 13, 2019   (CN) .......................... 201910742830.4

(51) Int. Cl.
*G01N 33/00*   (2006.01)
*E21B 49/08*   (2006.01)
(Continued)

(52) U.S. Cl.
CPC ......... *G01N 33/0036* (2013.01); *E21B 49/08* (2013.01); *E21F 17/00* (2013.01);
(Continued)

(58) Field of Classification Search
CPC ......... E21B 49/08; E21F 17/00; G01D 21/02; G01L 19/0618; G01L 5/047;
(Continued)

(56) References Cited

U.S. PATENT DOCUMENTS

| 2013/0036811 A1* | 2/2013 | Boult ...................... E21B 49/08 |
| | | 73/152.27 |
| 2014/0060811 A1* | 3/2014 | Mazyar ................. E21B 17/042 |
| | | 166/118 |
| 2017/0022809 A1* | 1/2017 | Garcia .................. E21B 49/088 |

FOREIGN PATENT DOCUMENTS

| DE | 4405976 A1 * | 3/1995 | ............. G01L 5/047 |
| KR | 101528831 B1 * | 6/2015 | |
| WO | WO-2019002901 A * | 1/2019 | ............. E21B 49/00 |

OTHER PUBLICATIONS

English machine translation for KR10-1528831 (Year: 2021).*
English machine translation for DE4405976 (Year: 2021).*

* cited by examiner

*Primary Examiner* — Peter J Macchiarolo
*Assistant Examiner* — Anthony W Megna Fuentes
(74) *Attorney, Agent, or Firm* — Carter, DeLuca & Farrell LLP (57) ABSTRACT

The present invention discloses a tunnel toxic-and-harmful-gas deep-hole detection device and method. The tunnel toxic-and-harmful-gas deep-hole detection device comprises a detector, a lifter, and a control terminal, which are sequentially connected. The control terminal controls the lifter to achieve movement of the lifter. The detector comprises a shell with a hollow interior and two opened ends. An air inlet is formed in the outer wall of the shell. A gas detector and a gas sampler are arranged in the shell, and the air inlet is located therebetween. The tunnel toxic-and-harmful-gas deep-hole detection method comprises two steps, namely a gas detection step and a gas sampling step. The present invention can effectively detect components and concentrations of various gases in a drill hole, wherein the detection data is real-time and accurate.

9 Claims, 3 Drawing Sheets

(51) Int. Cl.
  *E21F 17/00* (2006.01)
  *G01L 5/04* (2006.01)
  *G01L 19/06* (2006.01)
  *G01N 1/24* (2006.01)
  *G01N 1/22* (2006.01)
  *G01D 21/02* (2006.01)
(52) U.S. Cl.
  CPC .......... *G01L 5/047* (2013.01); *G01L 19/0618* (2013.01); *G01N 1/24* (2013.01)
(58) Field of Classification Search
  CPC .. G01N 1/2294; G01N 1/24; G01N 2001/245; G01N 33/0036; G01N 33/0062; G01N 33/0073
  See application file for complete search history.

TUNNEL TOXIC-AND-HARMFUL-GAS DEEP-HOLE DETECTION DEVICE AND METHOD

TECHNICAL FIELD

The present invention relates to the technical field of geological exploration drill hole detection, and specifically, to a tunnel toxic-and-harmful-gas deep-hole detection device and method.

BACKGROUND

Toxic and harmful gases severely threaten the tunnel engineering (for example, $CH_4$ and $H_2$ cause burning explosion, $H_2S$ and $SO_2$ cause people poisoning, and $CO_2$ cause people suffocating). So, the railway industry rules that the exploration and design stages of the railway tunnel must conduct the toxic and harmful gas evaluation, wherein detection on the toxic and harmful gas in an exploration drill hole is an important method for evaluating the tunnel toxic and harmful gas.

At present, a portable gas concentration detector is mainly used for detecting the components and the concentration of the gas in the opening of the tunnel exploration drill hole in the industry. Such detection method has the two defects: 1, gases $H_2S$ and $SO_2$ are heavier relative to the air, and they generally gather at the bottom of the drill hole, so, they cannot be effectively detected at the opening of the drill hole; 2, the relationship between the in-hole gas concentration and the drilling depth cannot be obtained. Therefore, it is necessary to develop a special device for detecting the toxic and harmful gas in the tunnel exploration hole.

SUMMARY

The present invention aims to solve a technical problem that the existing tunnel exploration drill hole gas detection is inaccurate, and the relationship between the gas concentration and the drilling depth cannot be obtained. The objective of the present invention is to propose a tunnel toxic-and-harmful-gas deep-hole detection device and method. The detection device and method cannot only effectively detect the components and the concentration of each gas in a drill hole, but also record the concentrations of the gas at different depths to obtain the relationship between the gas concentration and the drilling depth.

The present invention is achieved by the following technical solutions.

A tunnel toxic-and-harmful-gas deep-hole detection device comprises a detector, a lifter, and a control terminal, which are sequentially connected. The control terminal controls the lifter to achieve movement of the detector. At present, a portable gas concentration detector is mainly used for detecting the components and the concentration of gas in the opening of a tunnel exploration drill hole in the industry. Such detector has a small size, is convenient to carry and basically is handheld type. The detector is placed at the opening of the drill hole to detect. However, because there are multiple toxic and harmful gases, especially, $H_2S$, $SO_2$ and the like, and these gases are heavier relative to the air to gather at the bottom of the drill hole. So, the detection data is inaccurate and has a large error. Furthermore, the drilling depths are different during each exploration, so, the relationship between the gas in the drill hole and the drilling depth cannot be obtained and only depends on people to record, the amount of labor is large, the efficiency is low, and the error is easy to occur. The detection device of the present invention uses the control terminal to control the lifter to achieve the movement of the detector, and conducts the data transmission on all connected parts in a wire or wireless manner. The control terminal mainly is in charge of human-computer interaction. Various operation commands of the operator are sent out through the control terminal, and the control terminal reflects the working state and the detection data of the current device to the operator. The lifter is mainly used for controlling the in-hole detector to lift up and lift down and calculating the distance between the current in-hole detector and the opening of the drill hole. The in-hole detector is mainly in charge of detecting the components and the concentration of the gas in the exploration hole and can sample gas under the control of the control terminal. The detector can further detect the component and the concentration of the gas at different depths in the drill hole, and meanwhile, the control terminal collects the detection data to obtain the relationship between the gas concentration and the drilling depth.

Further, the detector comprises a shell with a hollow interior and two opened ends. The shell is connected with the lifter. An air inlet is formed in the outer wall of the shell. A gas detector and a gas sampler are arranged in the shell, and the air inlet is located therebetween. An exhaust net cover is mounted at one end of the shell and is fixed to its near end; the exhaust net cover is used for exhausting the gas which is pumped by the detection air pump and passes through the gas sensor. An exhaust end waterproof gas-permeable membrane is adhered to the inner wall of the exhaust net cover and is used for preventing water from entering the interior of the detection device through the exhaust net cover. A tension sensor is arranged in an inner cavity of the exhaust net cover. The tension sensor is fixed to the shell and is connected with a cable of the lifter. The cable is connected with the tension sensor and then fixed to the tail of the in-hole detector. When the in-hole detector normally lifts up or down, the tension sensor is tensioned. When the in-hole detector is stuck in a lifting process or is lifted down to the hole bottom, the tension sensor senses that the tension is suddenly reduced, even to zero, the tension sensor may feed back the state to the ground operator to conduct relative measures.

A guard net cover is mounted at the other end of the shell and fixed to its near end. The guard net cover adopts a water-permeable design. A level sensor is arranged in an inner cavity of the guard net cover. The guard net cover protects the level sensor, and the level sensor is used for detecting whether the end of the in-hole detector touches water. The air inlet is an air intake net cover. The air intake net cover is fixed to the shell and is communicated with the interior of the shell. The gases extracted by the detection air pump and the sampling air pump enter the pump through the air intake net cover. An air intake end waterproof gas-permeable membrane is arranged on the inner wall of the air intake net cover and is used for preventing water from entering the interior of the detection device through the air intake net cover.

The gas detection device comprises a detection air pump and a gas sensor. The detection air pump pumps the gas in the drill hole to the gas sensor for detection and analysis. The gas sensor is used for detecting the data including components, concentration, and the like of the gas. The gas sensor is mounted on an exhaust tube of the detection air pump. An air intake tube of the detection air pump faces to the air inlet; so, the accuracy of gas detection can be achieved.

The gas sampler comprises a sampling air pump, a gas pressure sensor, a one-way guide tube, and a gas sample bag.

An air intake tube of the sampling air pump faces to the air inlet. The one-way guide tube is arranged between the sampling air pump and the gas sample bag and is also communicated with an exhaust tube of the sampling air pump as well as the gas sample bag. The gas pressure sensor is located between the exhaust tube of the sampling air pump and the one-way guide tube and is also communicated with the exhaust tube of the sampling air pump as well as the one-way guide tube. The sampling air pump is used for extracting the gas in the hole to the gas sample bag. The gas pressure sensor is used for detecting the pressure of the gas in a sampling gas path. When the pressure of the gas achieves a preset value, the sampling gas pump is turned off. The one-way guide tube is used for preventing gas in the gas sample bag from reversely escaping after the sampling air pump is turned off. The gas sample bag is used for sampling the gas.

To achieve arrangement of the cable, a cable arranger and a speed and length sensor are mounted on the lifter. The cable arranger moves from side to side to uniformly wind the cable around a reel. The speed and length sensor is used for measuring take-up and payoff lengths and speeds of the cable. The cable of the lifter sequentially passes through the cable arranger and the speed and length sensor and then is connected with the detector.

A tunnel toxic-and-harmful-gas deep-hole detection method comprises gas detection and gas sampling, wherein the gas detection comprises the following steps:

(A), connecting the cable of the lifter with the detector, putting the detector into a drill hole, and adjusting its position rightly; powering on and turning on the detection device to ensure that the control terminal is in wireless communication with the lifter;

(B), preheating the gas sensor by the detector after the detection device is turned on, wherein a water touch fuse is automatically switched off at this time; switching on the water touch fuse to conduct gas detection after the preheating is completed;

(C), tightening the cable by the lifter, resetting the speed and length sensor, lifting down the detector at a preset speed by the lifter, and detecting the gas in the drill hole by the detector; when the detector is lifted down at each preset speed, sending a detection depth and a detected gas concentration to the control terminal, storing the data by the control terminal, and drawing a curve graph showing the relationship between the detection depth and the detected gas concentration on a screen by the control terminal;

(D), after the detector is lifted up to the opening of the drill hole, turning off a lifter motor, wherein at this time, the lifter sends a "test complete" status signal to the control terminal, the detection air pump stops working, the control terminal saves the collected detection data, and an operator exports the detection data.

The gas sampling comprises the following steps:

(a), firstly mounting an empty gas sample bag before the detection device is turned on;

(b), connecting the cable of the lifter with the detector, putting the detector into a drill hole, and adjusting its position rightly; powering on and turning on the detection device to ensure that the control terminal is in wireless communication with the lifter;

(c), preheating the gas sensor by the detector after the detection device is turned on, wherein the water touch fuse is automatically switched off at this time; switching on the water touch fuse to conduct gas sampling after the preheating is completed;

(d), lifting down or up the detector; sending a "sampling" command by the control terminal after the sampling depth is determined, wherein at this time, the sampling air pump in the detector starts inflating the gas sample bag, and the sampling air pump stops working after the gas pressure sensor senses that the gas sample bag is full; lifting up the detector to the opening of the drill hole, then completing the whole sampling operation.

In step (C), when the detected drill hole has underground water: after the level sensor touches the in-hole underground water, the level sensor sends a "water touch" status information to the control terminal, and simultaneously, the motor is controlled to lift up the detector at a preset speed. The detector still continuously conducts the gas detection and sends the detection depth and the detected gas concentration to the control terminal after lifting up at each preset height. The control terminal collects and updates the detection data, and then re-draws a curve graph showing the relationship between the detection depth and the detected gas concentration.

In step (C), when the detected drill hole does not have the underground water: after the detector touches the hole bottom, the tension sensor senses the sudden reduction of the tension force and sends a "bottom touch" status information to the control terminal, and simultaneously, the motor is controlled to lift up the detector at a preset speed. The detector still continuously conducts the gas detection and sends the detection depth and the detected gas concentration to the control terminal after lifting up at each preset height. The control terminal collects and updates the detection data, and then re-draws a curve graph showing the relationship between the detection depth and the detected gas concentration.

By utilizing the above method, the gas detection and the gas sampling can be conducted according to various situations in the drill hole. The control terminal draws the curve graph showing the relationship between the detection depth and the detected gas concentration to obtain the accurate and real-time detection data. The problem that the existing detector can only measure the gas in the opening of the drill hole and the accurate data cannot be obtained is solved. Furthermore, the curve graph is obtained by utilizing the preset program, which is convenient to count and analyze.

Compared with the prior art, the present invention has the following advantages and beneficial effects: the present invention cannot only effectively detect components and concentrations of various gases in the drill hole, wherein the detection data is real-time and accurate. It can also record the concentrations of the gases at different depths, determine the relationship between the gas concentration and the drilling depth, is professional in the industry of tunnel toxic and harmful gas evaluation, is used for detecting the concentrations of toxic and harmful gases in a drill hole during geological exploration, and is applicable to evaluation of tunnel toxic and harmful gases in the railway, highway and urban rail transit.

BRIEF DESCRIPTION OF THE DRAWINGS

The accompanying drawings described here are provided for further understanding of the embodiments of the present invention, and constitute a part of the present invention, but do not constitute limitations to the present invention. In the drawings.

Reference signs and corresponding components in the drawings:

1—detector, 2—cable, 3—pulley, 4—lifter, 5—wireless transmission, 6—control terminal, 7—in—hole underground water, 8—exhaust net cover, 9—exhaust end waterproof gas—permeable membrane, 10—tension sensor, 11—connection plug, 12—gas sensor, 13—detection air pump, 14—air inlet net cover, 15—air intake end waterproof gas—permeable membrane, 16—sampling air pump, 17—gas pressure sensor, 18—one—way guide tube, 19—gas sample bag, 20—detector control part, 21—level sensor, 22—guard net cover, 23—motor, 24—reel, 25—cable arranger, 26—lead screw, 27—belt, 28—lifter control part, 29—speed and length sensor, 30—touch screen, 31—gas detection indicator light, 32—sampling indicator light, 33—lifting wheel, 34—bottom touch indicator light, 35—water touch indicator light, 36—automatic gas detection button, 37—sampling button, 38—water touch fuse.

DESCRIPTION OF THE EMBODIMENTS

To make the objectives, technical solutions, and advantages of the present invention clearer, the following further describes the present invention in detail with reference to the embodiments and the accompanying drawings. The schematic embodiments of the present invention and the description thereof are intended to be illustrative of the present invention and do not constitute a limitation of the present invention.

Embodiment 1

As shown in FIG. 1 to FIG. 4, a tunnel toxic-and-harmful-gas deep-hole detection device comprises a detector 1, a lifter 4, and a control terminal 6, which are sequentially connected. The detector 1 is used for detecting the components and the concentration of gas in a drill hole and sampling the gas. The detector 1 and the lifter 4 are connected by utilizing a self-supporting cable 2 and a pulley 3. The self-supporting cable 2 consists of a wire cable and electric wires, is utilized as the power line and the signal line of the in-hole detector, and is also utilized for supporting the in-hole detector. The pulley 3 changes the traction direction of the self-supporting cable 2. The control terminal 6 sends an operation command, displays the working state, and displays and saves the detection data. The control terminal 6 controls the lifter 4 to achieve movement, detection and sampling of the detector 1. The lifter 4 and the control terminal 6 transmit signals through wireless transmission 5. The lifter 4 and the control terminal 6 utilize wireless data transmission; so, the flexibility of arrangement of ground devices, such as the lifter, the control terminal, and the like, can be improved. The detector 1 adopts a shell structure with a hollow interior and two opened ends. An exhaust net cover 8 is mounted at the top of the shell. The bottom of the exhaust net cover 8 is screwed down and fixed to the top of the shell. An exhaust end waterproof gas-permeable membrane 9 is adhered to the inner wall of the exhaust net cover 8 and is used for preventing water from entering the interior of the device through the exhaust net cover 8. Furthermore, a tension sensor 10 is arranged in an inner cavity of the exhaust net cover 8. The self-supporting cable 2 of the lifter 4 is connected with the tension sensor 10 and then is fixed to the end part of the detector. When the detector normally lifts up or down, the tension sensor 10 is tensioned. When the detector 10 is stuck in a lifting process or is lifted down to the hole bottom, the tension sensor 10 senses that the tension is suddenly reduced, even to zero, the tension sensor may feed back the state to the ground operator to conduct relative measures. A mounting board may be arranged in the inner cavity of the exhaust net cover 8. The tension sensor 10 is fixed to the top of the mounting board. A connection plug 11 is arranged at the bottom of the mounting board and is used for connecting a lower pipeline.

Figure 2:
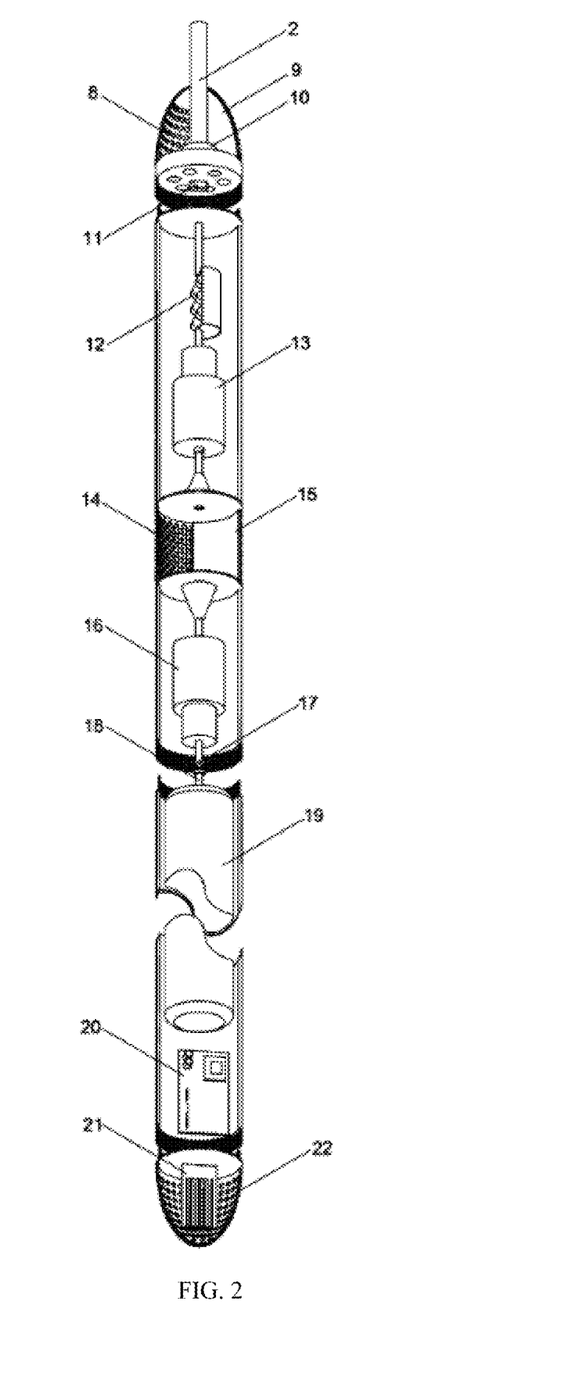
FIG. 2 is a schematic structural diagram of an in-hole detector of the present invention.

A guard net cover 22 is mounted at the bottom of the shell. The top of the guard net cover 22 and the bottom of the shell are screwed down and fixed. A level sensor 21 is arranged in the inner cavity of the guard net cover 22. The lever sensor 21 is used for detecting whether the end of the detector touches the water. The guard net cover 22 utilizes a water-permeable design and is used for protecting the level sensor 21.

To help the gas to enter the shell, an air inlet is arranged on the outer wall of the shell. The air inlet is an air intake net cover 14. The air intake net cover 14 is fixed to the shell and is communicated with the interior of the shell. An air intake end waterproof air-permeable membrane 15 is arranged on the inner wall of the air intake net cover 14 and is used for preventing the water from entering the interior of the detection device through the air intake net cover.

A gas detector and a gas sampler are arranged in the shell, and the air intake net cover 14 is located therebetween. The gas detector comprises a detection air pump 13 and a gas sensor 12. The gas sensor 12 is used for detecting data including the components and the concentration of the gas. The detection air pump 13 pumps the gas in the drill hole to the gas sensor 12 for detection and analysis. To achieve that the gas flows as required, the gas sensor 12 is mounted on an exhaust tube of the detection air pump 13. The exhaust tube is communicated with the inner cavity of the exhaust net cover 8 to exhaust the gas after the connection plug 11 is connected. However, an air intake tube of the detection air pump 13 faces to the air inlet and is used for smoothly guiding the gas.

The gas sampler comprises a sampling air pump 16, a gas pressure sensor 17, a one-way guide tube 18, and a gas sample bag 19. An air intake tube of the sampling air pump 16 faces to the air inlet. The one-way guide tube 18 is arranged between the sampling air pump 16 and the air sample bag 19 and is also communicated with an exhaust tube of the sampling air pump 16 as well as the gas sample bag 19. The gas pressure sensor 17 is located between the exhaust tube of the sampling air pump 16 and the one-way guide tube 18 and is also communicated with the exhaust tube of the sampling air pump 16 as well as the one-way guide tube 18. The sampling air pump 16 is used for extracting the gas in the hole to the gas sample bag 19. The gas pressure sensor 17 is used for detecting the pressure of the gas in a sampling gas path. When the pressure of the gas achieves a preset value, the sampling gas pump 16 is turned off. The one-way guide tube 18 is used for preventing gas in the gas sample bag 19 from reversely escaping after the sampling air pump 16 is turned off. The gas sample bag 19 is used for sampling the gas. A detector control part 20 is further arranged in the shell and is used for executing ground commands, controlling all parts of the detector to work, and arranging and transmitting the data. Such control part is the existing part, and it and its preset programs can be directly bought on the market.

Figure 3:
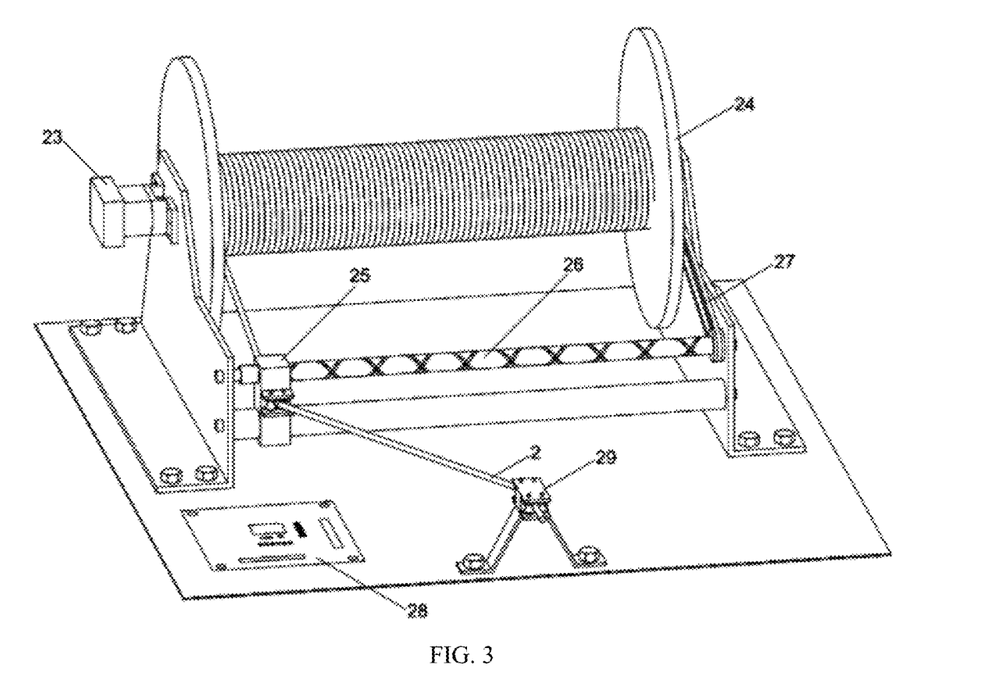
FIG. 3 is a schematic structural diagram of a lifter of the present invention.

In the lifter 4, the cable 2 winds around a reel 24. The lifter 4 comprises a base plate. Two supports are arranged on the base plate. The reel 24 is located between the two supports and is connected with the supports. The reel 24 can rotate around its axis between the supports. One support is equipped with a motor 23. The rotating shaft of the motor 23 is fixed to the reel 24 and is used for driving the reel 24 to rotate and providing power for the lifter. A cable arranger 25 and a speed and length sensor 29 are mounted on the base plate. The speed and length sensor 29 is used for measuring take-up and payoff lengths and speeds of the cable. A lead screw 26 is arranged between the supports. The lead screw 26 is connected with the supports at the same time. The lead screw 26 can rotates around its axis between the supports. The cable arranger 25 sleeves the lead screw 26. When the lead screw rotates, the cable arranger may do reciprocating movement along the lead screw. The cable arranged 25 moves side to side such that the self-supporting cable uniformly winds around the reel. The lead screw 26 and the reel 24 are connected through a belt 27. when the reel rotates, the reel drives the lead screw to rotate together. In use, the cable 2 of the lifter 4 should sequentially pass through the cable arranger 25 and the speed and length sensor 29. A lifter control part 28 is mounted on the base plate and is used for controlling all parts of the lifter. It is utilized as the data transit between the in-hole detector and the control terminal. Such control part is the existing part, and it and its preset programs can be directly bought on the market.

Figure 4:
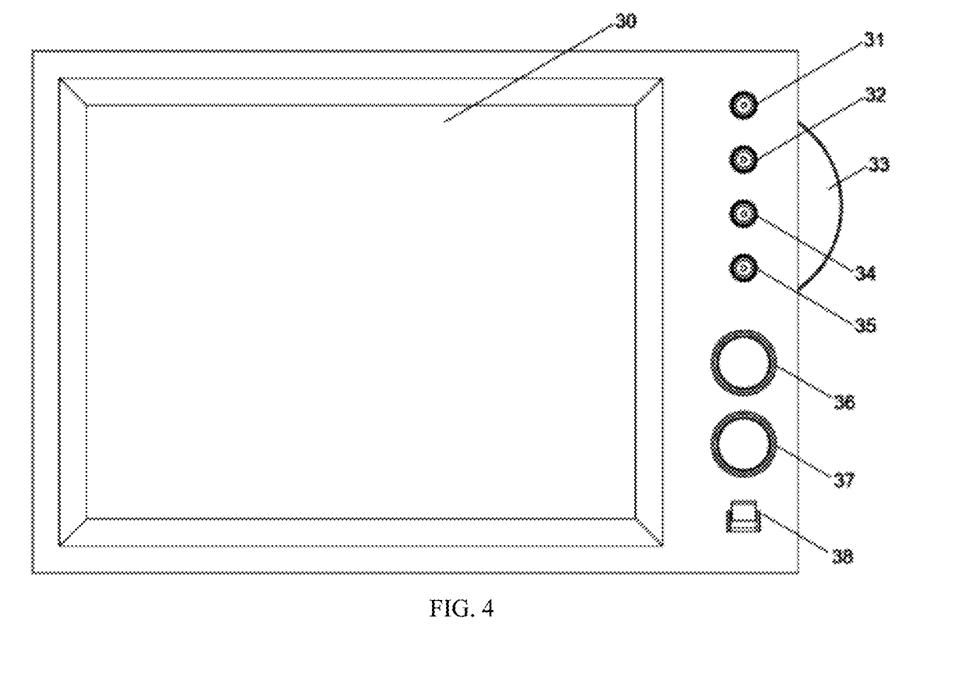
FIG. 4 is a schematic diagram of a control terminal of the present invention.

A touch screen 30 is arranged at the control terminal 6. The touch screen 30 is used for displaying the working state and the detection data and configuring the system. The control terminal 6 is further configured with a gas detection indicator light 31, a sampling indicator light 32, a bottom touch indicator light 34, a water touch indicator light 35, an automatic gas detection button 36, a sampling button 37, and a water touch fuse 38. The gas detection indicator light 31 lights in an automatic gas detection process. The sampling indicator light 32 lights in a sampling process. The bottom touch indicator light 34 lights when the tension sensor detects an abnormal tension force. The water touch indicator light 35 lights when the lever sensor touches the water. After the automatic gas detection button 36 is pressed down, the device automatically detects the gas in the drill hole according to the preset flow. After the sampling button 37 is pressed down, the gas is sampled. After the level sensor detects that the end of the in-hole detector touches the water, the water touch fuse 38 automatically switches off, and at this time, the lifter only receivers the lift-up command, but not the lift-down command. When an operator pushes up and down the lifting wheel 33 on the control terminal 6, the lifter is controlled to lift up and down. Furthermore, the larger the pushing range is, the higher the lifting up and down speeds are.

Figure 1:
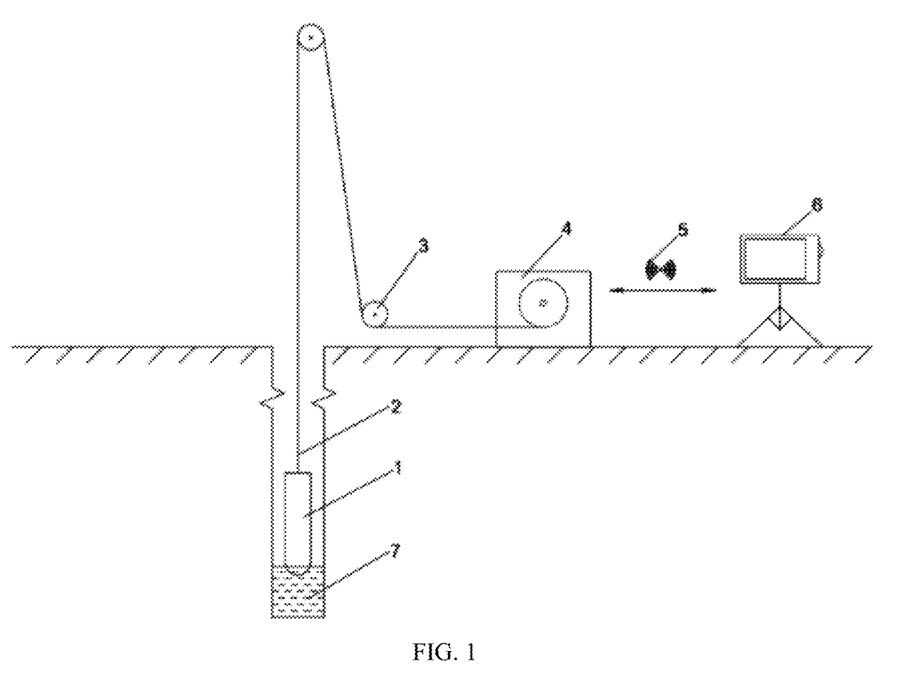
FIG. 1 is a schematic diagram showing assembly of a system of the present invention.

When the toxic and harmful gas in an exploration hole is fully automatically detected, the process is as follows:

Firstly, the head of the cable 2 is pulled out of the lifter 4. The cable 2 is connected with the in-hole detector 1. The in-hole detector 1 is put into the drill hole, and the positions of the pulley 3 and the lifter 4 are set. After the device is powered on and turned on, the control terminal 6 automatically conducts wireless communication with the lifter 4. After the device is ready, the touch screen 30 of the control terminal displays a ready icon. Device assembly is shown in FIG. 1.

After turning on, the in-hole detector 1 preheats the gas sensor 12, the control terminal 6 displays "device preheating" words, and at this time, the device cannot be operated. Moreover, the water touch fuse 38 automatically switches off After the control terminal 6 prompts "preheating complete", the operator should firstly pushes a switch of the water touch fuse 38 upwards, then presses down the automatic gas detection button 36 on the control terminal 6 to control the device to conduct the full automatic detection of the toxic and harmful gas in the drill hole.

When the gas detection starts, the cable 2 of the lifter 4 is firstly tightened, the speed and length sensor 29 resets, and the lifter 4 lifts down the in-hole detector 1 at the speed of 0.05 m/s (which can be set by the control terminal). The in-hole detector 1 starts continuously detecting the gas in the drill hole. When the in-hole detector 1 reduces to every 1 m (which can be set by the control terminal), that is, the current detected gas concentration is sent to the lifter through the self-supporting cable 2. The lifter 4 immediately sends the detection depth and the detected gas concentration to the control terminal 6. The control terminal 6 stores the data and draws a curve graph showing the relationship between the detection depth and the detected gas concentration on a screen.

When the detected drill hole has underground water: after the level sensor 21 in the guard net cover 22 at the end of the in-hole detector touches the in-hole underground water 7, the in-hole detector 1 sends "water touch" status information to the lifter 4. The lifter 4 forwards the "water touch" status information to the control terminal, and simultaneously controls the motor 23 to lift up the detector at the speed of 0.05 m/s (which can be set by the control terminal). At this time, the water touch indicator light 35 on the control terminal lights. The in-hole detector 1 still continuously conducts the gas detection, and sends the current detected gas concentration to the lifter 4 through the self-supporting cable 2 when the detectors 1 lifts up at every 1 m (which can be set by the control terminal). The lifter 4 immediately sends the detection depth and the detected gas concentration to the control terminal 6. The control terminal 6 collects and updates the detection data, and then re-draws a curve graph showing the relationship between the detection depth and the detected gas concentration.

When the detected drill hole does not have the underground water: when the in-hole detector 1 touch the hole bottom, the tension force of the tension sensor 10 is suddenly reduced, even to zero. The in-hole detector 1 immediately sends "bottom touch" status information to the lifter. The lifter 4 forwards the "bottom touch" status information to the control terminal, and simultaneously, controls the motor 23 to lifts up the detector at the speed of 0.05 m/s (which can be set by the control terminal). The bottom touch indicator light 34 of the control terminal lights, the in-hole detector 1 still continuously conducts the gas detection, and sends the current detected gas concentration to the lifter 4 through the self-supporting cable 2 when the detectors 1 lifts up at every 1 m (which can be set by the control terminal). The lifter 4 immediately sends the detection depth and the detected gas concentration to the control terminal. The control terminal 6 collects and updates the detection data, and then re-draws a curve graph showing the relationship between the detection depth and the detected gas concentration.

After the in-hole detector is lifted up to the opening of the drill hole, the motor 23 is turned off, and the lifter sends a "test complete" status signal to the control terminal. The control terminal controls the detection air pump 13 to stop working, and saves the collected detection data. The operator can connect the control terminal 6 with a computer through an USB line to export the detection data.

Embodiment 2

The structure in the embodiment and Embodiment 1 are basically the same, and their difference lies in: in the gas sampling process, an empty gas sample bag 19 should be firstly mounted before the detection device is turned on. Firstly, the head of the cable 2 is pulled out of the lifter 4. The cable 2 is connected with the in-hole detector 1. The in-hole detector 1 is put into the drill hole, and the positions of the pulley 3 and the lifter 4 are set. After the device is powered on and turned on, the control terminal 6 automatically conducts wireless communication with the lifter 4. After the device is ready, the touch screen 30 of the control terminal displays a ready icon. Device assembly is shown in FIG. 1. After turning on, the in-hole detector 1 preheats the gas pressure sensor 17, the control terminal 6 displays "device preheating" words, and at this time, the device cannot be operated. Moreover, the water touch fuse 38 automatically switches off After the device is turned on, the water touch fuse 38 defaults to be off, and at this time, the operator cannot control the lifter to lift down the in-hole detector through the lifting wheel 33; so, before sampling, the water touch fuse should be firstly switched on.

The operator lifts down or up the in-hole detector 1 through the lifting wheel 33; in such process, the control terminal 6 displays the relationship between the detection depth and the detected gas concentration in real time. After determining the sampling depth, the operator presses down the sampling button 37, the control terminal 6 sends a "sampling" command, and the in-hole detector 1 receives the "sampling" command and then opens the sampling air pump 16 to inflate the gas sample bag 19. After the gas pressure sensor 17 senses that the gas sample bag 19 is full, the sampling air pump 16 stops working. Due to the one-way guide tube 18, the gas in the gas sample bag 19 does not reversely escape. After the sampling is completed, the in-hole detector 1 sends "sampling complete" state information to the control terminal 6, and the control terminal 6 receives the information and then prompts the operator on the screen. The operator lifts up the in-hole detector to the opening of the drill hole through the lifting wheel. Until now, the whole sampling operation is completed.

Furthermore, to avoid that the in-hole detector is immersed into the underground water due to manual misoperation, the control terminal of the present invention is provided with the water touch fuse. When the level sensor 21 at the head of the in-hole detector touches the underground water, the water touch fuse immediately switches off. Before the fuse is manually switched on, the lifting control pulley can only control the in-hole detector to lift up, but not lift down.

The above specific embodiments further describe the objectives, technical solutions, and advantages of the present invention in detail. It should be understood that the above merely describes specific embodiments of the present invention, but the protection scope of the present invention is not limited thereto. Any modifications, equivalent substitutions, improvements, and the like within the spirit and principles of the present invention are intended to be included within the protection scope of the present invention.

What is claimed is:

1. A tunnel toxic-and-harmful-gas deep-hole detection device, comprising a detector (1), a lifter (4), and a control terminal (6), which are sequentially connected, wherein the control terminal (6) controls the lifter (4) to achieve movement of the detector (1);

wherein the detector (1) comprises a shell with a hollow interior and two opened ends; the shell is connected with the lifter (4); an air inlet is formed in the outer wall of the shell; a gas detector and a gas sampler are arranged in the shell, and the air inlet is located therebetween; and wherein an exhaust net cover (8) is mounted at one end of the shell; the exhaust net cover (8) is fixed to its near end; an exhaust end waterproof gas-permeable membrane (9) is adhered to the inner wall of the exhaust net cover (8); a tension sensor (10) is arranged in an inner cavity of the exhaust net cover (8); and the tension sensor (10) is fixed to the shell and is connected with a cable (2) of the lifter (1).

2. The tunnel toxic-and-harmful-gas deep-hole detection device according to claim 1, wherein a guard net cover (22) is mounted at an other end of the shell; the guard net cover (22) is fixed to its near end; and a level sensor (21) is arranged in an inner cavity of the guard net cover (22).

3. The tunnel toxic-and-harmful-gas deep-hole detection device according to claim 1, wherein the gas detector comprises a detection air pump (13) and a gas sensor (12); the gas sensor (12) is mounted at an exhaust tube of the detection air pump (13); and an air intake tube of the detection air pump (13) faces to the air inlet.

4. The tunnel toxic-and-harmful-gas deep-hole detection device according to claim 1, wherein the gas sampler comprises a sampling air pump (16), a gas pressure sensor (17), a one-way guide tube (18), and a gas sample bag (19); an air intake tube of the sampling air pump (16) faces to the air inlet; the one-way guide tube (18) is arranged between the sampling air pump (16) and the gas sample bag (19) and is also in communication with an exhaust tube of the sampling air pump (16) as well as the gas sample bag (19); the gas pressure sensor (17) is located between the exhaust tube of the sampling air pump (16) and the one-way guide tube (18) and is also in communication with the exhaust tube of the sampling air pump (16) as well as the one-way guide tube (18).

5. The tunnel toxic-and-harmful-gas deep-hole detection device according to claim 1, further comprising a cable arranger (25) and a speed and length sensor (29), wherein the cable (2) of the lifter (4) sequentially passes through the cable arranger (25) and the speed and length sensor (29) and then is connected with the detector (1).

6. A tunnel toxic-and-harmful-gas deep-hole detection method, comprising gas detection and gas sampling, wherein the gas detection performed by a detection device comprises the following steps:

(A), connecting a cable (2) of a lifter (4) with a detector (1), putting the detector (1) into a drill hole, and adjusting its position rightly; powering on and turning on the detection device to ensure that the control terminal (6) is in wireless communication with the lifter (4);

(B), preheating a gas sensor (12) by the detector (1) after the detection device is turned on, wherein a water touch fuse (38) is automatically switched off at this time;

switching on the water touch fuse (38) to conduct gas detection after the preheating is completed;

(C), tightening the cable by the lifter (4), resetting a speed and length sensor (29), lowering down the detector (1) at a preset speed by the lifter (4), and detecting the gas in the drill hole by the detector (1); when the detector (1) is lowered down at each preset speed, sending detection depth data and detected gas concentration data to the control terminal (6), storing the data by the control terminal (6), and drawing a curve graph showing the relationship between the detection depth data and the detected gas concentration data on a screen by the control terminal;

(D), after the detector (1) is lifted up to the opening of the drill hole, turning off a lifter motor (23), wherein at this time, the lifter sends a "test complete" status signal to the control terminal (6), the detection air pump (13) stops working, the control terminal (6) saves the collected detection data, and an operator exports the detection data;

the gas sampling comprises the following steps:

(a), firstly mounting an empty gas sample bag (19) before the detection device is turned on;

(b), connecting the cable of the lifter (4) with the detector (1), putting the detector (1) into a drill hole, and adjusting its position rightly; powering on and turning on the detection device to ensure that the control terminal (6) is in wireless communication with the lifter (4);

(c), preheating a gas pressure sensor (17) by the detector (1) after the detection device is turned on, wherein the water touch fuse (38) is automatically switched off at this time; switching on the water touch fuse (38) to conduct gas sampling after the preheating is completed;

(d), lowering down or lifting up the detector (1); sending a "sampling" command by the control terminal (6) after the sampling depth is determined, wherein at this time, a sampling air pump (16) in the detector (1) starts inflating the gas sample bag (19), and the sampling air pump (16) stops working after the gas pressure sensor (17) senses that the gas sample bag (19) is full; lifting up the detector (1) to the opening of the drill hole, then completing the whole sampling operation.

7. The tunnel toxic-and-harmful-gas deep-hole detection method according to claim 6, wherein in step (C), when the detected drill hole has underground water: after a level sensor (21) touches the in-hole underground water (7), the level sensor sends a "water touch" status information to the control terminal (6), and simultaneously, a motor (23) is controlled to lift up the detector at a preset speed; the detector (1) still continuously conducts the gas detection and sends the detection depth data and the detected gas concentration data to the control terminal (6) after lifting up the detector to preset heights; the control terminal (6) collects and updates the detection data, and then re-draws a curve graph showing the relationship between the detection depth data and the detected gas concentration data.

8. The tunnel toxic-and-harmful-gas deep-hole detection method according to claim 6, wherein in step (C), when the detected drill hole does not have the underground water: after the detector (1) touches the hole bottom, a tension sensor (10) senses the sudden reduction of the tension force and sends a "bottom touch" status information to the control terminal (6), and simultaneously, a motor (23) is controlled to lift up the detector at a preset speed; the detector (1) still continuously conducts the gas detection and sends the detection depth data and the detected gas concentration data to the control terminal (6) after lifting up the detector to preset heights; the control terminal (6) collects and updates the detection data, and then re-draws a curve graph showing the relationship between the detection depth data and the detected gas concentration data.

9. A tunnel toxic-and-harmful-gas deep-hole detection device, comprising a detector (1), a lifter (4), and a control terminal (6), which are sequentially connected, wherein the control terminal (6) controls the lifter (4) to achieve movement of the detector (1);

wherein the detector (1) comprises a shell with a hollow interior and two opened ends; the shell is connected with the lifter (4); an air inlet is formed in the outer wall of the shell; a gas detector and a gas sampler are arranged in the shell, and the air inlet is located therebetween;

wherein a guard net cover (22) is mounted at an other end of the shell; the guard net cover (22) is fixed to its near end; and a level sensor (21) is arranged in an inner cavity of the guard net cover (22).

\* \* \* \* \*